(12) United States Patent
Rudolph et al.

(10) Patent No.: US 7,297,676 B2
(45) Date of Patent: Nov. 20, 2007

(54) THYMOSIN ALPHA 1 PEPTIDE/POLYMER CONJUGATES

(75) Inventors: Alfred R. Rudolph, Los Altos Hills, CA (US); Cynthia W. Tuthill, Menlo Park, CA (US)

(73) Assignee: SciClone Pharmaceuticals, Inc., San Mateo, CA (US)

( * ) Notice: Subject to any disclaimer, the term of this patent is extended or adjusted under 35 U.S.C. 154(b) by 0 days.

(21) Appl. No.: 10/493,690

(22) PCT Filed: Nov. 1, 2002

(86) PCT No.: PCT/US02/35094

§ 371 (c)(1),
(2), (4) Date: Jul. 9, 2004

(87) PCT Pub. No.: WO03/037272

PCT Pub. Date: May 8, 2003

(65) Prior Publication Data

US 2004/0248792 A1    Dec. 9, 2004

Related U.S. Application Data

(60) Provisional application No. 60/330,870, filed on Nov. 1, 2001.

(51) Int. Cl.
*A61K 38/17* (2006.01)
(52) U.S. Cl. .......................................... 514/2; 530/399
(58) Field of Classification Search ...................... None
See application file for complete search history.

(56) References Cited

U.S. PATENT DOCUMENTS

| | | | |
|---|---|---|---|
| 4,079,127 A * | 3/1978 | Goldstein et al. | 514/12 |
| 4,179,337 A * | 12/1979 | Davis et al. | 435/181 |
| 4,353,821 A | 10/1982 | Birr et al. | |
| 4,766,106 A * | 8/1988 | Katre et al. | 514/12 |
| 4,917,888 A | 4/1990 | Katre et al. | |
| 5,122,614 A | 6/1992 | Zalipsky | |
| 5,595,732 A | 1/1997 | Hakini et al. | |
| 5,632,983 A | 5/1997 | Hadden | |
| 6,177,074 B1 | 1/2001 | Glue et al. | |
| 6,309,633 B1 * | 10/2001 | Ekwuribe et al. | 424/85.1 |
| 2005/0114037 A1 | 5/2005 | Desjarlais et al. | |

FOREIGN PATENT DOCUMENTS

| | | |
|---|---|---|
| CN | 10654565 A | 10/1992 |
| WO | WO 94/13314 A1 | 6/1994 |
| WO | WO 95/13090 | 5/1995 |

OTHER PUBLICATIONS

File Hcaplus on STN, DN No. 118:167075. Knusli et al. Polyethylene glycol (PEG) modification of granulocyte-macrophage colony stimulating factor (GM-CSF) enhances neutrophil priming activity but not colony stimulating activity. British Journal of Haematology (1992), 82(4), 654-63 (abstract only).*

File Hcaplus on STN, DN No. 123:81299. Tsutsumi et al. Molecular design of hybrid tumor necrosis factor alpha with polyethylene glycol increases its anti-tumor potency. British Journal of Cancer (1995), 71(5), 963-8 (abstract only).*

Chiu, H. et al., "Enzymatic activity of chymotrypsin and its poly-(ethylene glycol) conjugates toward low and high molecular weight substrates,", *Bioconjugate Chem.* 1993, 4;290-295.

Schiavon, O., et al., "Therapeutic proteins: a comparison of chemical and biological properties of uricase conjugated to linear or branched poly(ethylene glycol) and poly(N-acryloylmorpholine)", *Il Farmaco* 2000,55:264-269.

Rodrigues, P., et al., "Acid-sensitive polyethylene glycol conjugates of doxorubicin: preparation, in vitro efficacy and intracellular distribution", *Bioorg Med Chem.* 1999;7:2517-2524.

Nodake, Y., et al., "Some properties of a macromolecular conjugate of lysozyme prepared by modification with a monomethoxypolyethylene glycol derivative", *Biosci Biotechnol Biochem.* 2000;64:767-774.

Grace, M. et al., "Site of pegylation and polyethylene glycol molecule size attenuate interferon-alpha antiviral and antiproliferative activities through the JAK/STAT signaling pathway", *J. Biol Chem.* 2005;280:6327-6336.

Bailon, P. et al., "Rational design of a potent, long-lasting form of interferon: a 40 kDa branched polyethylene glycol-conjugated interferon alpha-2a for the treatment of hepatitis C", *Bioconjug Chem.* 2001;12:195-202 (1 page).

Wang, Y.S. et al., "Structural and biological characterization of pegylated recombinant interferon alpha-2b and its therapeutic implications", *Adv Drug Deliv Rev.* 2002;54:547-570 (1 page).

*Queensborough Community College: The City University of New York*, The New York Chemistry Students' Association, Student Affiliate Committee—New York Section (American Chemical Society), May 1, 2004, 1-46, (Huang et al., p. 30).

Clinical application and foreground of Thymosin a1 in treating virus hepatitis, 2000, Section of Virology Foreign Medical Sciences (7)6:168-171.

* cited by examiner

*Primary Examiner*—Anish Gupta
(74) *Attorney, Agent, or Firm*—Rothwell Figg Ernst & Manbeck, P.C.

(57) ABSTRACT

A pharmaceutical composition includes a physiologically active conjugate including a Thymosin alpha 1 (TA1) peptide conjugated to a material which increases half-life of the TA1 peptide in serum of a patient when the conjugate is administered to a patient. The material may be a substantially non-antigenic polymer. In a method of the invention, the substantially non-antigenic polymer is conjugated to a TA1 peptide. Compositions according to the invention are administered to patients in need of immune stimulation.

31 Claims, No Drawings

THYMOSIN ALPHA 1 PEPTIDE/POLYMER CONJUGATES

CROSS-REFERENCE TO RELATED APPLICATION

This application is a National Stage of International Application No. PCT/US02/35094, filed Nov. 1, 2002, which claims the benefit of U.S. Provisional Application No. 60/330,870, filed Nov. 1, 2001.

BACKGROUND OF THE INVENTION

1. Field of the Invention

The present invention relates to Thymosin alpha 1 peptides.

2. Description of the Background Art

Thymosin alpha 1 (sometimes referred to as TA1) is a 28-amino acid thymic peptide with immunomodulatory properties, homologous to a natural product originally isolated from thymosin fraction 5 of calf thymus. Its biological effects include augmentation of T lymphocyte functions and include modulation of interleukin-2 (IL-2), stimulation of interferon-γ production, induction of T lymphocytes and NK cell activity, and stimulation of thymopoiesis. Thymosin alpha 1 also has been shown to up-regulate MHC Class I expression.

There remains a need in the art for improved compositions containing TA1 and related peptides.

SUMMARY OF THE INVENTION

A pharmaceutical composition in accordance with the present invention comprises a physiologically active conjugate comprising a Thymosin alpha 1 (TA1) peptide conjugated to a material which increases half-life of the TA1 peptide in serum of a patient when said conjugate is administered to a patient. The material may be a substantially non-antigenic polymer. According to a method of the invention, a substantially non-antigenic polymer is conjugated to a TA1 peptide. Compositions in accordance with the present invention are administered to patients in need of immune stimulation.

DETAILED DESCRIPTION OF THE INVENTION

The present invention is applicable to TA1 peptides including naturally occurring TA1 as well as synthetic TA1 and recombinant TA1 having the amino acid sequence of naturally occurring TA1, amino acid sequences substantially similar thereto, or an abbreviated sequence form thereof, and their biologically active analogs having substituted, deleted, elongated, replaced, or otherwise modified sequences which possess bioactivity substantially similar to that of TA1, e.g., a TA1 peptide having sufficient amino acid homology with TA1 such that it functions in substantially the same way with substantially the same activity as TA1.

A pharmaceutical composition in accordance with the present invention comprises a physiologically active conjugate comprising a TA1 peptide conjugated to a material which increases half-life of the TA1 peptide in serum of a patient when said conjugate is administered to a patient. The material may be a substantially non-antigenic polymer. Suitable polymers will have a molecular weight within a range of about 200-300,000, preferably within a range of about 1,000-100,000, more preferably within a range of about 5,000-35,000, and most preferably within a range of about 10,000-30,000, with a molecular weight of about 20,000 being particularly preferred.

The polymeric substances included are also preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Among the substantially non-antigenic polymers, mono-activated, alkyl-terminated polyalkylene oxides (PAO's), such as monomethyl-terminated polyethylene glycols (mPEG's) are contemplated. In addition to mPEG, $C_{1-4}$ alkyl-terminated polymers may also be useful.

As an alternative to PAO-based polymers, effectively non-antigenic materials such as dextran, polyvinyl pyrrolidones, polyacrylamides, polyvinyl alcohols, carbohydrate-based polymers and the like can be used. Those of ordinary skill in the art will realize that the foregoing list is merely illustrative and that all polymer materials having the qualities described herein are contemplated. For purposes of the present invention, "effectively non-antigenic" means all materials understood in the art as being nontoxic and not eliciting an appreciable immunogenic response in mammals.

The polymer may be straight-chain or branched. Polyethylene glycol (PEG) is a particularly preferred polymer.

The polymer can be conjugated to the TA1 peptide by any suitable method. Exemplary methods for conjugating polymers to peptides are disclosed in U.S. Pat. Nos. 4,179,337, 4,766,106, 4,917,888, 5,122,614 and 6,177,074, as well as PCT International Publication No. WO 95/13090, all of which are incorporated herein by reference. Thymosin alpha 1 has five separate possible sites for amino group conjugation of a polymer, and polymer(s) can be conjugated at one or a plurality of sites. According to one embodiment, 20,000 molecular weight PEG is conjugated to the N-terminal end of TA1 to form a PEG-TA1. This can be formed by solid phase peptide synthesis of TA1 on insoluble polymeric support beads, as is known in the art, with appropriate side chain protective groups. After complete synthesis of the TA1 peptide on the beads, the protected TA1 is cleaved from the beads leaving the N-terminus with a free amino group, which is reacted with 20,000 molecular weight PEG. The side chain protective groups then are removed to form a conjugate in accordance with this embodiment of the invention.

Compositions in accordance with the present invention may be utilized to treat patients in need of immune stimulation. Such patients may include cancer patients, hepatitis patients including patients infected with Hepatitis B or Hepatitis C virus, HIV patients, etc. The method involves administering to a patient an immune stimulated-effective amount of a physiologically active conjugate in accordance with the present invention.

The isolation, characterization and use of TA1 peptides is described, for example, in U.S. Pat. No. 4,079,127, U.S. Pat. No. 4,353,821, U.S. Pat. No. 4,148,788 and U.S. Pat. No. 4,116,951. Immune stimulating-effective amounts of TA1 peptide can be determined by routine dose-titration experiments. TA1 has been found to be safe for humans when administered in doses as high as 16 mg/kg body weight/day. Preferred dosages of TA1 peptide are within the range of 0.001 mg/kg body weight/day to 10 mg/kg body weight/day, with an exemplary dose being about 0.02 mg/kg body weight/day. According to one embodiment, immune stimulating-effective amounts are at dosages which include the TA1 peptide in an amount within a range of about 0.1-10 mg. Preferred dosages include the TA1 peptide in an amount within the range of about 1-5 mg. The above dosages reflect only the TA1 peptide present in the composition, and not the weight of the polymer conjugated thereto.

In preferred embodiments, the TA1 peptide is present in a pharmaceutically acceptable liquid carrier, such as water for injection, saline in physiologic concentrations, or similar.

The plasma half-life of subcutaneously injected TA1 is only about 2 hours. However, conjugation of a polymer to a TA1 peptide in accordance with the present invention substantially increases the plasma half-life of the peptide.

The invention is further illustrated by the following examples which are not intended to be limiting.

EXAMPLE 1

Rats were injected with 5-fluorouracil (5-FU) to cause immune suppression, then were treated with an injection of thymosin alpha 1 (200 ug/kg) or pegylated thymosin alpha 1 (20,000 MW PEG-Thymosin alpha 1) (the equivalent on a molar basis of 200 ug/kg of thymosin molecules) to determine the effect on immune parameters. It was found that: (1) the return of NK activity (after depression by 5-FU) was greater in animals injected with PEG-Thymosin alpha 1 than with Thymosin alpha 1, and (2) the return of activated T cells, CD25+, was greater for animals injected with PEG-Thymosin alpha 1 than with Thymosin alpha 1.

In the following examples, which are not intended to be limiting, a continuous infusion of TA1 was evaluated in a cancer therapy model with the use of surgically implanted osmotic minipumps, which deliver fluids at a constant flow rate for 5 days. Rats were given 5-fluorouracil (5-FU) to cause immune suppression, and then treated with injected or infused TA1 8 days later (the nadir of white cell count after 5-FU). Treatment groups, 8 rats each, were: control (minipumps with saline); low dose TA1 (0.2 mg/Kg sc injection; empty minipumps); high dose TA1 (3.5 mg/Kg sc injection; empty minipumps); and high dose infused TA1 (3.5 mg/Kg infused by minipumps). Immune parameters were determined at baseline and 8 days after 5-FU treatment (day 1 of TA1 treatment), and also at 5, 12, 20, and 27 days after TA1 treatment.

EXAMPLE 2

10 week old rats, weighing 250-300 g, received 100 mg/kg 5-fluorouracil (5-FU) for immune suppression.

8 days after 5-FU treatment, rats were randomly assigned to one of the following groups (n=8):
Control (saline in minipump)
Low dose TA1, injected s.c. at 0.2 mg/Kg (with empty minipumps)
High dose TA1, injected s.c. at 3.5 mg/Kg (with empty minipumps)
Continuous infusion TA1, provided by minipump at 3.5 mg/Kg/5 days Immune parameters were determined at baseline and 8 days after 5-FU treatment (day 1 of TA1 treatment), and also at 5, 12, 20, and 27 days after TA1 treatment.

The evaluations included NK activity (LDH released from YAC-1 cells after 4 h exposure to PBMC), total leukocyte number (judged by physical cytofluorimetric parameters, after verifying the specificity by monoclonal antibody), total lymphocyte number (CD3+ by flow cytometry), and activated lymphocytes (CD25+CD3+ by flow cytometry).

NK activity was 42±5% at baseline and was depressed to 9±2% after 5-FU. Low dose TA1 treatment lead to a significant recovery of NK activity after 12 days, while high dose TA1 achieved significant recovery in only 5 days. Continuous infusion of TA1, however, was able to double the response at 5 days, to 32±4% (versus 16±2 for high dose injected, 12±3 low dose injected, and 11±1 control). Only animals treated with TA1 by continuous infusion had a complete recovery of NK activity to baseline levels.

Total white blood cell count, as determined by morphology, was depressed from 14,590±2,071 cells/mm$^3$ to 2,597±582 after treatment with 5-FU. Low or high dose TA1 treatment trended towards a sooner increase in recovery compared to untreated animals. Continuous infusion of TA1, however, provided statistically significant and complete recovery to baseline levels after only 5 days.

Activated lymphocytes (CD3+CD25+) were not decreased significantly by 5-FU treatment (from 65±21 cells/mm$^3$ to 37±10), however, the levels were dramatically increased 12 and 20 days after high dose TA1 treatment (297±136 and 321±75 cells/mm$^3$ vs 166±70 and 212±77 cells/mm$^3$, respectively). TA1 provided by continuous infusion lead to an even greater increase, to 422±105 and 446±73 cells/mm$^3$.

EXAMPLE 3

10 week old rats, weighing 250-300 g, received 100 μg/kg 5-FU for immune suppression.

8 days after 5-FU treatment, rats were randomly assigned to one of the following groups (n=15):
Control (saline in minipump)
High dose TA1, injected s.c. at 3.5 mg/Kg (with empty minipumps)
Continuous infusion TA1, provided by minipump at 3.5 mg/Kg/5 days Immune parameters were determined at baseline and 8 days after 5-FU treatment (day 1 of TA1 treatment), and also at 5 and 14 days after TA1 treatment.

The evaluations included total leukocyte number (judged by physical cytofluorimetric parameters, after verifying the specificity by monoclonal antibody), granulocytes (flow cytometry using FITC anti rat granulocyte HIS-48), total lymphocyte number (CD3+ by flow cytometry), T helper lymphocytes (CD4+ by flow cytometry), activated lymphocytes (CD25+CD3+ by flow cytometry), and cytokine expression in plasma (IL-2 and IFN-γ by ELISA).

After determining in Example 2 that TA1 provided by continuous infusion compared to s.c. injection had a dramatic effect on the total number of leukocytes, it was of interest to determine which type of white blood cell was responsible for the increase. Granulocytes appear to be the subset of white blood cells that are most affected by TA1 provided by continuous infusion. The number of granulocytes was decreased after 5-FU from 4,485±1,116 to 1,249±432. Treatment with TA1 resulted in an increase to 14,652±2,463 within 5 days (compared to 9,924±3,218 with TA1 by injection or 6,954±1,519 with no TA1), and this level was still the highest after 14 days.

Interestingly, there was one animal in this study which was provided TA1 by BOTH injection (of 3.5 mg/Kg) and by continuous infusion (of another 3.5 mg/Kg). Not only was this animal healthy and vigorous, with no obvious adverse events, but the TA1 effects on the immune parameters measured were even greater than those in the other animals. For granulocytes, this study animal had a greatly increased level of 19,376 cells/mm³ after 5 days, compared to the mean of 14,652±2,463 in the other infused animals.

The number of total lymphocytes (CD3+) was dramatically decreased by 5-FU treatment (from 10,904±1,973 cells/mm³ to 1,740±560). Treatment with TA1 allowed for a recovery to baseline levels, which occurred after only 5 days when TA1 was provided by continuous infusion but was not seen until 14 days for injected TA1.

The animal that had TA1 provided by both injection and infusion had levels of lymphocytes which were not much different from the other animals (9,765 cells/mm³ compared to the mean of 9,644±961), but the percentage of these lymphocytes which were activated was greatly increased (from 428±89, or 4% of lymphocytes, for the animals with TA1 by infusion, to 976, or 10% of lymphocytes, for the animal which had TA1 in a high dose injection followed by infusion).

T helper lymphocytes (CD3+CD4+) were also depressed by treatment with 5-FU, from 5,411±1,084 cells/mm³ to 1,710±449. These depressed levels of T cells did not increase without treatment with TA1 for the 14 days of the experiment. By contrast with the results seen for granulocytes, in which TA1 provided by continuous infusion was superior to TA1 provided by injection for recovery of cell numbers, TA1 provided by either delivery method was sufficient to return the levels of T helper cells to baseline.

Since TA1 provided either by injection or by continuous infusion lead to an increase in CD4+ T helper lymphocytes, it was of interest to determine whether this increase was due to an effect on the Th1 or the Th2 subset of T helper cells. Previous in vitro and in vivo data have demonstrated that TA1 increases the Th1 subset of T cells, and in this study the same effect was seen. Providing TA1 by continuous infusion lead to an even greater increase in the plasma level of the Th1 cytokine IL-2 than was seen after s.c. injection (42±7 pg/ml 14 days after TA1 by continuous infusion, compared to 21±16 for injected TA1 and 10±16 for control animals).

Treatment by TA1 lead to an increase in the Th1 cytokine IL-2, and TA1 allows for an increase in another Th1 cytokine, IFN-γ. Although the levels are low, by 5 days after treatment, s.c. injected TA1 lead to higher plasma levels of IFN-γ. By 14 days after treatment the animals with TA1 provided by continuous infusion had the highest levels (14±5 pg/ml compared to 10±1 by injection or 8±8 for control).

The animal which received TA1 by both injection and continuous infusion had even greater levels of both of the Th1 cytokines measured, especially IFN-γ, which was 45 pg/ml after 14 days, compared to 14±5 pg/ml for the other animals.

CONCLUSIONS

Maintenance of a constant level of TA1 over a plurality of days in the circulation increases the measured immunological effects.

This dosage regimen leads to unexpected positive effects on granulocytes, as well as the positive effects on monocytes seen after injection of TA1.

No adverse events were observed, even at doses of TA1 15 times higher than usual (and in one animal, at doses 30 times higher than usual).

The invention claimed is:

1. A pharmaceutical composition comprising a physiologically active conjugate, said conjugate comprising a Thymosin alpha 1 (TA1) peptide conjugated to a material which increases the half-life of the TA1 peptide in serum of a patient when said conjugate is administered to a patient, wherein said material which increases half-life is a polyalkylene oxide polymer.

2. The composition of claim 1 wherein said material is a substantially non-antigenic polymer.

3. The composition of claim 2 wherein said polymer is PEG.

4. The composition of claim 3 wherein said PEG has a molecular weight within a range of about 200-300,000.

5. The composition of claim 4 wherein said molecular weight is about 5,000-35,000.

6. The composition of claim 5 wherein said molecular weight is about 20,000.

7. The composition of claim 2 wherein said polymer is conjugated to an N-terminal portion of the TA1 peptide.

8. The composition of claim 1 wherein said TA1 peptide is TA1.

9. A method of forming a composition as claimed in claim 2, comprising conjugating a substantially non-antigenic polymer to a Thymosin alpha 1 peptide.

10. The method of claim 9 wherein the polymer is conjugated to an N-terminal portion of the Thymosin alpha 1 peptide.

11. The method of claim 9 wherein the polymer is PEG.

12. The method of claim 9 wherein said PEG has a molecular weight in a range of about 200-300,000.

13. The method of claim 12 wherein said molecular weight is about 5,000-35,000.

14. The method of claim 13 wherein said molecular weight is about 20,000.

15. The method of claim 9 wherein said Thymosin alpha 1 peptide is TA1.

16. A pharmaceutical composition comprising a physiologically active conjugate, said conjugate comprising Thymosin alpha 1I (TA1) peptide conjugated to a substantially non-antigenic PEG which increases the half-life of the TA1 peptide in serum of a patient when said conjugate is administered to a patient.

17. The composition of claim 16 wherein said PEG has a molecular weight within a range of about 200-300,000.

18. The composition of claim 17 wherein said molecular weight is about 5,000-35,000.

19. The composition of claim 18 wherein said molecular weight is about 20,000.

20. The composition of claim 16 wherein said PEG is conjugated to an N-terminal portion of the TA1 peptide.

21. The composition of claim 16 wherein said TA1 peptide is TA1.

22. A method of forming a composition as claimed in claim 16, comprising conjugating substantially non-antigenic PEG to a Thymosin alpha 1 peptide.

23. The method of claim 22 wherein the PEG is conjugated to an N-terminal portion of the Thymosin alpha 1 peptide.

24. The method of claim 23 wherein said PEG has a molecular weight in a range of about 200-300,000.

25. The method of claim 24 wherein said molecular weight is about 5,000-35,000.

26. The method of claim 25 wherein said molecular weight is about 20,000.

27. The method of claim 22 wherein said Thymosin alpha 1 peptide is TA1.

28. The composition of claim 1, wherein said material which increases half-life is conjugated to the N-terminal end of said peptide.

29. The method of claim 15, wherein said material which increases half-life is conjugated to the N-terminal end of said peptide.

30. A composition comprising a conjugate, said conjugate comprising a Thymosin alpha 1 peptide having a PEG with a molecular weight of about 20,000 conjugated to the N-terminal end of said peptide.

31. A pharmaceutical composition comprising a physiologically active conjugate, said conjugate comprising a Thymosin alpha 1 (TA1) peptide conjugated to a PEG having a molecular weight of about 20,000 conjugated to the N-terminal end of said peptide.

* * * * *